(12) United States Patent
Buisine

(10) Patent No.: US 9,394,225 B2
(45) Date of Patent: Jul. 19, 2016

(54) METHOD FOR PROCESSING FLUORIC ACID

(71) Applicant: RHODIA OPERATIONS, Paris (FR)

(72) Inventor: Olivier Buisine, Saint Genis-Laval (FR)

(73) Assignee: RHODIA OPERATIONS, Paris (FR)

(*) Notice: Subject to any disclaimer, the term of this patent is extended or adjusted under 35 U.S.C. 154(b) by 0 days.

(21) Appl. No.: 14/429,442

(22) PCT Filed: Sep. 17, 2013

(86) PCT No.: PCT/EP2013/069267
§ 371 (c)(1),
(2) Date: Mar. 19, 2015

(87) PCT Pub. No.: WO2014/053312
PCT Pub. Date: Apr. 10, 2014

(65) Prior Publication Data
US 2015/0232408 A1    Aug. 20, 2015

(30) Foreign Application Priority Data
Oct. 3, 2012  (FR) ...................... 12 59372

(51) Int. Cl.
*C07C 67/08*  (2006.01)
(52) U.S. Cl.
CPC ..................... *C07C 67/08* (2013.01)
(58) Field of Classification Search
None
See application file for complete search history.

(56) References Cited

U.S. PATENT DOCUMENTS

| 4,879,407 A | * | 11/1989 | Amiet ........................ 560/227 |
| 5,591,877 A | | 1/1997 | Obermeier et al. |
| 2011/0166385 A1 | | 7/2011 | Buisine et al. |

FOREIGN PATENT DOCUMENTS

| EP | 0267127 A1 | 5/1988 |
| EP | 1514848 A1 | 3/2005 |
| EP | 2298726 A1 | 3/2011 |
| JP | 2008162902 * | 7/2008 |
| WO | WO 2008078479 A1 | 7/2008 |
| WO | WO 2010003986 A1 | 1/2010 |
| WO | WO 2012062602 A1 | 5/2012 |

OTHER PUBLICATIONS

Machine Translation obtained from << worldwide.espacenet.com>>.*
Perry, R.H. et al.—Perry's Chemical Engineers' Handbook, 4th Edition, (1973) Section 23, p. 44 (2 pages).
Non-machine English language translation of JP 2008162902, translation provided by RWS Group.

* cited by examiner

*Primary Examiner* — Karl J Puttlitz

(57) ABSTRACT

The present invention relates to a method for processing an aqueous solution containing a salt of an organic compound including at least one acid function and at least one fluorine atom, or fluoric acid, by reaction between said salt and at least one Bronsted acid and an alcohol in the presence of an organic solvent solubilizing the resulting product, wherein said organic solvent consists of at least one dual-phase liquid/liquid reaction medium with the aqueous solution.

16 Claims, No Drawings

METHOD FOR PROCESSING FLUORIC ACID

CROSS-REFERENCE TO RELATED APPLICATIONS

The present application is a U.S. national stage entry under 35 U.S.C. §371 of International Application No. PCT/EP2013/069267 filed Sep. 17, 2013, which claims priority to FR Application No. 12 59372 filed on Oct. 3, 2012 and, the whole content of this application being herein incorporated by reference for all purposes.

The present invention relates to a process for treating a fluoro acid, especially a fluoro acetic acid, for example difluoroacetic acid (DFA) or trifluoroacetic acid (TFA), and especially to a process for treating a fluoro acid in salified form in an aqueous solution.

DFA may be produced via various processes and, depending on the process, may be found dissolved in an aqueous solution in the form of a salt, especially the sodium salt. DFA, even after acidification, is soluble in aqueous solution; this consequently makes its recovery, for example by distillation or extraction, very difficult.

There is thus a need to provide a process for treating fluoro acids that are soluble in aqueous phase and in particular DFA or TFA, especially when they are in the form of salts in an aqueous solution.

The object of the present invention is to provide a process for treating a fluoro acid, especially a process for treating a salt of a fluoro acid in aqueous solution, in particular DFA or TFA.

Another object of the present invention is to provide such a process that is easy to perform and that can produce an upgradable product in good yields and with a high purity.

The process of the present invention makes it possible to overcome the various abovementioned problems.

The inventors have discovered, surprisingly, that it is possible to treat an aqueous solution containing a salt of a fluoro acid that is soluble in aqueous phase, by esterification of this salt in acidic medium.

However, if the esterification of the salt of the fluoro acid, especially of DFA or TFA, is performed directly in the aqueous solution by adding an acid and the desired alcohol, immediately upon formation, the ester, which is a strong acid ester, becomes hydrolyzed. It is therefore not possible via this method to recover an ester of a fluoro acid, especially of DFA or TFA, in good yields.

The process of the invention also makes it possible to solve this technical problem.

The present invention relates to a process for treating an aqueous solution comprising a salt of an organic compound comprising at least one acid function and at least one fluorine atom, referred to as a fluoro acid, by reaction between said salt and at least one Brönsted acid in the presence of an organic solvent that dissolves the formed product, said organic solvent forming at least a liquid/liquid two-phase reaction medium with the aqueous solution. In the context of the invention, the fluoro acid is especially chosen from water-soluble fluoro carboxylic acids. Preferably, the acid is chosen from aliphatic carboxylic acids comprising at least one fluorine atom and comprising from 2 to 15 carbon atoms and preferably from 2 to 10 carbon atoms. Preferential examples that may be mentioned include fluoro acetic acids.

In the context of the present invention, the term "fluoro acetic acid" denotes mono-, di- and trifluoroacetic acids and any mixtures thereof, preferably di- and trifluoroacetic acids, more particularly difluoroacetic acid.

In one particular embodiment, the aqueous solution comprising the fluoro acid salt is an aqueous solution derived from a process for preparing said acid.

In another embodiment, the aqueous solution comprising the fluoro acid salt is an effluent, the fluoro acid then being a by-product to be upgraded.

As indicated previously, the fluoro acid is in salified form in the aqueous solution; the counterion may especially be chosen from elements of columns 1 to 12 of the Periodic Table of the Elements, and the counterion is preferably an alkali metal or an alkaline-earth metal, for example sodium, potassium or lithium.

The aqueous solution of fluoro acid salt may also comprise one or more mineral salts, especially of formula MX in which X is a halogen atom, especially fluorine or chlorine, and M is an element chosen from elements of columns 1 to 12 of the Periodic Table of the Elements, and preferably M is an alkali metal or an alkaline-earth metal, for example sodium, potassium or lithium. These salts may be included in the aqueous solution in a proportion of from 5% to 80% by weight relative to the total weight of the aqueous solution comprising the salt of the fluoro acid. The presence of these mineral salts in addition to the salt of the fluoro acid has the consequence of increasing the density of the aqueous phase. The choice of the organic solvent from among the abovementioned solvents is then made as a function of the density of the aqueous medium comprising the salt of the salified fluoro acid.

The term "at least a liquid/liquid two-phase reaction medium" denotes a medium comprising two liquid phases, on the one hand the organic solvent phase and on the other hand the aqueous phase, such a medium also possibly comprising solid compounds in suspension, for instance precipitated salts.

The term "Brönsted acid" means a molecule that is capable of yielding one or more protons.

Preferably, a Brönsted acid according to the invention is chosen from strong acids whose pKa is less than 2, and in particular from HCl, $H_2SO_4$, $HNO_3$, HBr or $H_3PO_4$, in pure or diluted form, or any mixture thereof. Hydrochloric acid may be used in gaseous form and/or as a solution (aqueous solution). Preferably, the acid is used in proportions of from 1 to 5 molar equivalents and preferably from 1 to 3 molar equivalents relative to the salt of the fluoro acid.

The reaction of the fluoro acid salt with the Brönsted acid affords the corresponding fluoro acid.

Advantageously, the product formed from the reaction between the fluoro acid salt and the Brönsted acid is dissolved by the organic solvent.

The organic solvent is preferably a water-immiscible solvent, thus making it possible to form a reaction medium that is at least a liquid/liquid two-phase medium before and after reaction of the fluoro acid salt with at least one Brönsted acid.

Although the organic solvent may be used in any proportion, it is preferably used in proportions of from 50% to 200% and preferably from 50% to 100% by volume relative to the volume of the aqueous solution.

The process of the invention may be performed at a temperature of from 10° C. to 100° C. and preferably from 20° C. to 80° C.

In one particular embodiment, the process of the invention is performed in batch mode.

In another particular embodiment, the process of the invention is performed continuously.

Preferably, the process of the invention is performed by placing the various phases of the reaction medium in intimate contact. One of the phases should then be finely dispersed in the other so as to increase the contact surface and consequently the reaction kinetics. This may be done via any method known to those skilled in the art.

In the context of a process performed in batch mode, it is preferable to use a reactor provided with a stirring system allowing vigorous stirring of the reaction medium, especially a reactor provided with a stirring system of 4-paddle type, especially with 4 inclined paddles; or of turbomixer type, for example a Rushton turbomixer.

The process according to the invention may also comprise at least one step of separating the organic solvent/formed product mixture from the aqueous solution, especially by settling of the phases.

The aqueous phase is recovered separately during this separation step. In one embodiment, this aqueous phase may be subjected to a new treatment process according to the invention for the purpose of converting the fluoro acid salts that have not yet been converted (several extraction stages).

In another embodiment, the recovered aqueous phase may optionally be subjected to one or more liquid/liquid extractions with the abovementioned solvents without further addition of reagents (several extraction stages).

In order to recover the formed product, the process of the invention may also comprise at least one step of distilling the organic solvent/formed product mixture derived from the separation step.

This distillation step may be performed via any method known to those skilled in the art. The size (especially the diameter) of the distillation columns depends on the stream circulating and on the internal pressure. They will therefore be sized mainly according to the flow rate of mixture to be treated. Preferably, all the distillations performed in the process of the invention are performed at atmospheric pressure.

Preferably, for this distillation step, the distillation column may advantageously, but not limitingly, be a column having the following specifications:

number of theoretical stages: from 3 to 30, preferably from 3 to 25;

reflux rate R: from 2 to 10.

In the context of a process performed continuously, it is preferable to use separation columns comprising from 2 to 50 theoretical stages and preferably from 2 to 30 theoretical stages, especially columns such as: packed columns; fixed or movable plate columns; rotary disk columns; columns with agitated compartments, for instance Kuhni columns; pulsed columns, for example perforated-disk pulsed columns; or batch reactors as described above placed in series with an overflow system allowing continuous passage from one reactor to another.

This distillation step may be preceded by a flash distillation step for obtaining an organic medium that is concentrated in formed product. This flash distillation step is preferably performed at atmospheric pressure, in a distillation column comprising less than 10 theoretical stages, with a flux rate R of less than 5.

The process according to the invention is preferably performed in installations capable of withstanding the corrosiveness of the reaction medium. It is thus possible to use alloys based on molybdenum, chromium, cobalt, iron, copper, manganese, titanium, zirconium, aluminum, carbon and tungsten, sold under the Hastelloy® brand name or the alloys of nickel, chromium, iron and manganese to which copper and/or molybdenum are added, sold under the name Inconel®, and more particularly the Hastelloy C 276 or Inconel 600, 625 or 718 alloys. Stainless steels may also be selected, such as austenitic steels [Robert H. Perry et al., *Perry's Chemical Engineers' Handbook, Sixth Edition* (1984), pages 23-44] and more particularly the 316 or 316 L stainless steels. A steel having a nickel content of at most 22% by mass, preferably of between 6% and 20% and more preferably of between 8% and 14%, is used. Steels 316 and 316L have a nickel content ranging between 10% and 14%. The material may also be chosen from graphite materials and fluoro polymers, and derivatives thereof. Among the fluoro polymers, PTFE (polytetrafluoroethylene), PVDF (polyvinylidene fluoride) and PFAs (perfluoroalkyl resins) are particularly suitable for performing the process of the invention. Finally, the material may be vitrified steel.

The choice of material will depend on the reaction medium and on the salts which it may contain; a person skilled in the art is capable of determining these materials with his general knowledge. The materials that are particularly preferred are vitrified steel and fluoro polymers.

The organic solvent is chosen from solvents for dissolving the formed product, but which subsequently allow its separation, for example by distillation. Thus, and preferably, the organic solvent is chosen from solvents with a boiling point that is sufficiently remote from the boiling point of the formed product to allow separation, especially by distillation. The organic solvent used for the process of the invention may be a mixture of organic solvents.

Advantageously, the organic solvent is chosen from apolar solvents. Preferably, the organic solvent is chosen from aromatic solvents, halogenated and preferably chlorinated aliphatic solvents, or alkyl ethers, preferably C1 to C15 and preferably C1 to C10 alkyl ethers, or mixtures thereof.

The term "aromatic solvent" denotes solvents bearing an aromatic ring, for example phenyl, optionally substituted with one or more groups chosen especially from linear or branched alkyl groups comprising from 1 to 10 carbon atoms and preferably from 1 to 5 carbon atoms; halogen atoms, preferably chlorine; -Oalkyl groups with alkyl being linear or branched and comprising from 1 to 10 carbon atoms and preferably from 1 to 5 carbon atoms. Preferably, the aromatic solvent is chosen from xylene (ortho, meta or para), toluene, chlorobenzene, dichlorobenzene, mesitylene, methoxybenzene (anisole), 1,2-dimethoxybenzene (veratrole), ethylbenzene, trifluoromethylbenzene, or any mixture thereof.

The term "halogenated aliphatic" means a linear or branched alkyl chain comprising from 1 to 10 carbon atoms and preferably from 1 to 5 carbon atoms, and being substituted with one or more halogen atoms, especially chlorine. Preferably, the organic solvent is chosen from dichloromethane, dichloroethane and chloroform, or any mixture thereof.

The term "alkyl ether" denotes linear or branched alkyl ethers, preferably comprising from 2 to 15 carbon atoms, for example from 2 to 10 carbon atoms. Preferably, the alkyl ether is chosen from methyl tert-butyl ether (MTBE) and diisobutyl ether, or a mixture thereof.

The process of the invention may also comprise the reaction of the fluoro acid salt with the Brönsted acid and an alcohol to produce the corresponding ester.

Thus, the products formed via the process of the invention are especially the fluoro acid or the ester of the fluoro acid.

In one particular embodiment, the invention relates to a process for treating an aqueous solution comprising a fluoro acid salt by reaction between said salt and a Brönsted acid in the presence of an organic solvent that dissolves the formed product, said organic solvent forming at least a liquid/liquid two-phase reaction medium with the aqueous solution.

The fluoro acid salt, the Brönsted acid and the organic solvent are as defined above. Preferably, the organic solvent is chosen from aromatic solvents, especially substituted with one or more -Oalkyl groups with alkyl being linear or branched and comprising from 1 to 10 carbon atoms and preferably from 1 to 5 carbon atoms; or alkyl ethers. Preferably, the solvent is methoxybenzene (anisole), 1,2-dimethoxybenzene (veratrole), MTBE or diisobutyl ether.

This embodiment may advantageously be performed using a fluoro acetic acid salt, and especially using a DFA salt.

In a particularly preferred embodiment, the invention relates to a process for treating an aqueous solution comprising a fluoro acid salt by reaction between said salt, a Brönsted acid and an alcohol in the presence of an organic solvent that dissolves the formed ester, said organic solvent forming at least a liquid/liquid two-phase reaction medium with the aqueous solution.

The fluoro acid salt is as defined above. This embodiment is particularly suited to fluoro aliphatic carboxylic acid salts as defined above and especially to fluoro acetic acid salts and more particularly to DFA salts.

Such a process makes it possible, surprisingly, to obtain good yields for the conversion of the fluoro acid salt and good yields in terms of production of ester of this acid. The process of the invention makes it possible to obtain a fluoro acid ester in a purity of greater than 90%, preferably greater than 95% and more preferably close to 99%. Moreover, the yield for the conversion of the fluoro acid salt via the process of the invention is greater than 80% and preferably greater than 90%. The yield of fluoro acid ester is greater than 80% and preferably greater than 90%.

In a particular embodiment, the process of the invention relates to a process for treating a DFA salt and for producing a DFA ester. All of the variants and embodiments apply in particular to DFA.

Preferably, the alcohol according to the invention is a water-soluble alcohol which has a low molecular mass. Preferably, the alcohol according to the invention is an alcohol of formula $R^1OH$ in which $R^1$ represents a linear or branched alkyl group comprising from 1 to 10 carbon atoms and preferably from 1 to 5 carbon atoms, for example methyl, ethyl, propyl, isopropyl, butyl, pentyl and isopentyl. Preferably, the alcohol is chosen from methanol, ethanol and isopropanol, and the ester formed is then the ethyl, methyl or isopropyl ester of difluoroacetic acid. Particularly preferably, the alcohol is ethanol.

It is preferable for the amounts of alcohol to be controlled. Preferably, the alcohol is used in proportions of from 1 to 5 molar equivalents relative to the salt of the fluoro acetic acid, preferably from 1 to 4 molar equivalents.

Preferably, the organic solvent is chosen from solvents for dissolving the formed ester, but which subsequently allow its separation by distillation. Thus, and preferably, the organic solvent is chosen from solvents with a boiling point that is sufficiently remote from the boiling point of the formed fluoro acetic acid ester to allow separation of the organic solvent and of the ester, especially by distillation. Thus, and preferably, in particular in the case where the alcohol is ethanol, the organic solvent is chosen from organic solvents with a boiling point of less than or equal to 90° C., preferably from 30 to 90° C., or a boiling point of greater than or equal to 100° C., preferably from 100 to 200° C., for example from 110 to 180° C., measured at atmospheric pressure (101 325 Pa).

The organic solvent used for the reaction may be a mixture of solvents. According to a preferred variant, the ester formed is the ethyl ester of the fluoro acetic acid and the organic solvent is chosen from solvents that dissolve this ester.

Advantageously, the organic solvent is chosen from apolar solvents.

The various conditions described in the context of the process of the invention may be combined together.

Preferably, the solvent is chosen from aromatic solvents and chlorinated aliphatic solvents.

In one particular embodiment, in particular when the alcohol is ethanol, the organic solvent may be chosen from aromatic solvents with a boiling point of greater than or equal to 100° C., preferably from 100 to 200° C., for example from 110 to 180° C. The aromatic solvents defined above may be used. Preferably, the organic solvent is chosen from xylene (ortho, meta or para), toluene, chlorobenzene, dichlorobenzene, mesitylene, methoxybenzene (anisole), 1,2-dimethoxybenzene (veratrole), ethylbenzene, trifluoromethylbenzene, or any mixture thereof.

In another embodiment, in particular when the alcohol is ethanol, the organic solvent may be chosen from halogenated aliphatic solvents with a boiling point of less than or equal to 90° C., preferably from 30 to 90° C. The halogenated aliphatic solvents are especially defined above. Preferably, the organic solvent is chosen from dichloromethane, dichloroethane and chloroform, or any mixture thereof.

In another embodiment, in particular when the alcohol is ethanol, the organic solvent may be chosen from C2 to C15 and preferably C2 to C10 alkyl ethers.

In the embodiment in which the process uses an alcohol, the process according to the invention may also comprise at least one step of separating the organic solvent/formed acid ester mixture from the aqueous solution, especially by settling of the phases.

The aqueous phase is recovered separately during this separation step. In one embodiment, this aqueous phase may be subjected to a new treatment process according to the invention for the purpose of converting the fluoro acetic acid salts that have not yet been converted (several extraction stages).

In another embodiment, the recovered aqueous phase may optionally be subjected to one or more liquid/liquid extractions with the abovementioned solvents without further addition of alcohol (several extraction stages).

In order to recover the formed fluoro acid ester, the process of the invention may also comprise at least one step of recovering the fluoro acid ester by distillation of the organic solvent/fluoro acid ester mixture derived from the separation step.

This distillation step may be performed via any method known to those skilled in the art and especially according to the variants and embodiments described above.

In the case where the alcohol used is ethanol, the fraction whose boiling point is between 97 and 99° C. is recovered during this distillation; it corresponds to the fluoro acid ester fraction with a purity of greater than 90%, preferably greater than 95% and more preferably close to 99%.

Advantageously, the organic solvent fraction, obtained at the top of the column in the case of an organic solvent with a boiling point of less than 90° C., or obtained at the bottom of the column in the case of an organic solvent with a boiling point of greater than 100° C., may be recycled into the esterification step of the process of the invention.

Advantageously, the fractions containing the fluoro acid ester that are insufficiently pure and the alcohol may be recycled into the esterification step of the process of the invention.

This distillation step may be preceded by a flash distillation step for obtaining an organic medium that is concentrated in fluoro acetic acid ester. This flash distillation step is preferably performed at atmospheric pressure, in a distillation column comprising less than 10 theoretical stages, with a flux rate R of less than 5.

According to a particular embodiment, the invention relates to a process for preparing an ester from a fluoro acid using the process of the invention.

The present invention consequently also relates to a process for preparing a fluoro acid ester, comprising the treatment of an aqueous solution comprising a salt of an organic compound comprising at least one acid function and at least one fluorine atom, referred to as a fluoro acid, by reaction between said salt, an alcohol and at least one Brönsted acid in the presence of an organic solvent that dissolves the formed product, said organic solvent forming at least a liquid/liquid two-phase reaction medium with the aqueous solution.

The embodiments and preferred embodiments described above also apply to the process for preparing the fluoro acid ester.

The process of the present invention will now be described with the aid of nonlimiting examples. The temperature is expressed in degrees Celsius and is room temperature (20-25° C.), unless otherwise indicated. The pressure is atmospheric pressure, unless otherwise indicated.

EXAMPLE 1

574.7 g of an aqueous solution containing 14.4% by weight of sodium difluoroacetate and 9% by weight of sodium chloride and also 126 g of concentrated sulfuric acid at 98% by weight are placed in a glass reactor equipped with a jacket and a Rushton turbomixer. The sulfuric acid is added over 1 hour so as to keep the temperature below 50° C. After returning to room temperature, 207 g of xylene (mixture of o-, m- and p-isomers) and 39.7 g of ethanol are added. The medium is stirred at 850 rpm for 1 hour at room temperature. The stirring is then stopped and the upper organic phase is recovered by settling of the phases. Two further liquid/liquid extraction operations are performed using the aqueous solution obtained, with the addition of twice 207 g of xylenes.

The recovered organic phases are combined (m=720.1 g) and placed in a distillation boiler equipped with a column containing 20 theoretical stages. The distillation is performed at atmospheric pressure. The fraction with a boiling point of between 98° C. and 99° C. is collected. The fraction obtained m=70.1 g consists of DFAE in a purity of 98.7% by weight. The yield is 80%.

EXAMPLE 2

475.3 g of an aqueous solution containing 13% by weight of sodium difluoroacetate and also 165 g of concentrated sulfuric acid at 98% by weight are placed in a glass reactor equipped with a jacket and a Rushton turbomixer. The acid is added over 1 hour so as to keep the temperature below 50° C. After returning to room temperature, 224 g of o-dichlorobenzene and 45 g of ethanol are added. The medium is stirred at 850 rpm for 1 hour at room temperature. The stirring is then stopped and the lower organic phase is recovered by settling of the phases. A second liquid/liquid extraction operation is performed under the same conditions using the aqueous solution obtained previously, with addition of a further 201 g of dichlorobenzene. Analysis by $^1$H NMR and $^{19}$F NMR indicates that the conversion of the sodium difluoroacetate is 92%. Analysis by gas chromatography shows that 89% of the theoretical ethyl difluoroacetate is present in organic solution. These organic solutions obtained (m=500.3 g) are combined and distilled at atmospheric pressure on a column equipped with 20 theoretical stages, with a reflux rate ranging from 15 to 3. A 28.3 g fraction with a boiling point of between 97.5 and 99° C. is recovered. The ethyl difluoroacetate concentration is greater than 97% by weight. The reaction yield is 51%. A second distillation of this fraction makes it possible to obtain the ethyl difluoroacetate in a purity of greater than 99.5% by weight. This yield of 51% may be improved to more than 80% by recycling the impure fractions of DFA ester containing alcohol as explained above.

EXAMPLE 3

8.7 g of potassium difluoroacetate, 43.8 g of potassium fluoride, 6.3 g of potassium chloride and 115 g of concentrated 37% hydrochloric acid are added to a PTFE reactor equipped with a Rushton turbomixer. After returning to room temperature, 9 g of ethanol and 190 g of o-xylene are added and stirring is continued for 1 hour at 850 rpm. The upper phase is then recovered by settling of the phases. Two further liquid/liquid extractions of the aqueous phase are performed by adding twice 190 g of o-xylene. Measurement by $^1$H NMR and $^{19}$F NMR indicates that the degree of conversion of the potassium difluoroacetate present in the aqueous phase is 93%. Analysis of the organic phases by gas chromatography indicates that the yield of extracted ethyl difluoroacetate is 88%. The organic phases are combined and distilled at atmospheric pressure using a column comprising 20 theoretical stages. The fraction with a boiling point of between 98 and 98.5° C. is recovered. It corresponds to ethyl difluoroacetate having a purity of 99% by weight.

EXAMPLE 4

483 g of an aqueous solution containing 15% by weight of sodium trifluoroacetate and 165 g of concentrated sulfuric acid are placed in a glass reactor equipped with a Rushton turbomixer. The acid is added over 1 hour so as to keep the temperature below T=50° C. After returning to a temperature of 24° C., 190 g of o-xylene and 33 g of ethanol are added and the medium is kept stirring for 1 hour. After separation of the phases by settling, the organic (upper) phase is recovered and the aqueous phase is extracted a second time with 200 g of o-xylene. The two organic phases are combined. Analysis by gas chromatography shows that 83% of the expected ethyl trifluoroacetate is present in organic solution. This solution is distilled at atmospheric pressure on a column equipped with 20 theoretical stages. The fraction with a boiling point of between 60° C. and 62° C. is collected. The purity of the ethyl trifluoroacetate is 91% by weight.

EXAMPLE 5

30 g of concentrated (37%) hydrochloric acid solution, 13.6 g of ethanol and 70 g of p-xylene are added to a reactor containing 24.5 g of potassium 3,3,3-trifluoropropanoate and 38.7 g of potassium chloride dissolved in 217 mL of water. Stirring is maintained for 30 minutes at room temperature. The two phases are then separated and the aqueous phase is extracted twice more with 70 g of p-xylene. The organic layers are then combined. 347 g of an organic solution containing 6.1% by weight of ethyl 3,3,3-trifluoropropanoate are obtained.

EXAMPLE 6

Concentrated hydrochloric acid solution (363 g) is added to a solution of 81.4 g of 2-fluoropropanoic acid, 162 g of potassium fluoride and 65.9 g of potassium chloride in 249 g of water, while keeping the temperature below T=35° C. Methanol (59 g) and mesitylene (492 g) are then added and the mixture is stirred for 30 minutes. The phases are separated and the aqueous solution is extracted twice more with 492 g of mesitylene. All the organic solutions obtained are combined to give 1515 g of an organic solution containing 81.6 g of methyl 2-fluoropropanoate. The methyl 2-fluoropropanoate yield is 84%. This ester is obtained in pure form after distillation under reduced pressure.

The invention claimed is:

1. A process for treating an aqueous solution comprising a salt of an organic compound comprising at least one acid function and at least one fluorine atom, referred to as a fluoro acid, by reacting said salt in aqueous solution with at least one Bronsted acid and an alcohol selected from the group consisting of methanol, ethanol, and isopropanol in the presence of an organic solvent that dissolves the formed product, said organic solvent forming at least a liquid/liquid two-phase reaction medium with the aqueous solution, wherein the organic solvent is selected from the group consisting of aromatic solvents, chlorinated aliphatic solvents and alkyl ethers, and any mixture thereof.

2. The process as claimed in claim 1, in which the fluoro acid is chosen from water-soluble fluoro carboxylic acids.

3. The process as claimed in claim 1, in which the fluoro acid is chosen from aliphatic carboxylic acids comprising at least one fluorine atom and comprising from 2 to 15 carbon atoms.

4. The process as claimed in claim 1, in which the fluoro acid is a fluoro acetic acid.

5. The process as claimed in claim 1, in which the aqueous solution also comprises one or more mineral salts of formula MX, in which X is a halogen atom, especially fluorine or chlorine; and M is an element chosen from elements of columns 1 to 12 of the Periodic Table of the Elements.

6. The process as claimed in claim 1, in which the alcohol is ethanol.

7. The process as claimed in claim 1, in which the Bronsted acid is chosen from HCl in gaseous form or in solution, $H_2SO_4$, $H_3PO_4$, $HNO_3$ or HBr, in pure or diluted form, or any mixture thereof.

8. The process as claimed in claim 1, in which the aromatic solvent is selected from the group consisting of xylene (ortho, meta or para), toluene, chlorobenzene, dichlorobenzene, mesitylene, methoxybenzene (anisole), 1,2-dimethoxybenzene (veratrole), ethylbenzene, trifluoromethylbenzene, and any mixture thereof.

9. The process as claimed in claim 1, in which the chlorinated aliphatic solvent is selected from the group consisting of dichloromethane, dichloroethane and chloroform, and any mixture thereof.

10. The process as claimed in claim 1, for which the alkyl ether solvent is selected from the group consisting of methyl tert-butyl ether (MTBE) and diisobutyl ether, and a mixture thereof.

11. The process as claimed in claim 1, in which the alcohol is used in a proportion of from 1 to 5 molar equivalents relative to the fluoro acid salt.

12. The process as claimed in claim 1, in which the solvent is used in a proportion of from 50% to 200% by volume relative to the volume of the aqueous solution.

13. The process as claimed in claim 1, also comprising at least one step of separating the solvent/formed product mixture from the aqueous solution.

14. The process as claimed in claim 10, also comprising at least one step of recovering the formed product by distillation of the solvent/formed product mixture.

15. The process as claimed in claim 14, also comprising a step of flash distillation followed by a step of distillation.

16. The process as claimed in claim 1, in which the fluoro acid is difluoroacetic acid and the formed product is a difluoroacetic acid ester.

\* \* \* \* \*